United States Patent
Yamane et al.

(10) Patent No.: US 6,916,939 B2
(45) Date of Patent: Jul. 12, 2005

(54) PROCESS FOR THE PREPARATION OF CYCLIC ESTERS AND METHOD FOR PURIFICATION OF THE SAME

(75) Inventors: Kazuyuki Yamane, Fukushima (JP); Yukichika Kawakami, Fukushima (JP); Hajime Hoshi, Fukushima (JP); Kazuhiko Sunagawa, Fukushima (JP)

(73) Assignee: Kureha Kagaku Kogyo K.K., Tokyo (JP)

( * ) Notice: Subject to any disclaimer, the term of this patent is extended or adjusted under 35 U.S.C. 154(b) by 0 days.

(21) Appl. No.: 10/344,461

(22) PCT Filed: Aug. 8, 2001

(86) PCT No.: PCT/JP01/06816

§ 371 (c)(1),
(2), (4) Date: Feb. 11, 2003

(87) PCT Pub. No.: WO02/14303

PCT Pub. Date: Feb. 21, 2002

(65) Prior Publication Data

US 2003/0191326 A1 Oct. 9, 2003

(30) Foreign Application Priority Data

Aug. 11, 2000 (JP) ........................................ 2000-244449

(51) Int. Cl.[7] ............................................. C07D 319/12

(52) U.S. Cl. ........................................ 549/274; 203/39

(58) Field of Search ............................ 549/274; 203/39

(56) References Cited

U.S. PATENT DOCUMENTS

| | | | |
|---|---|---|---|
| 2,668,162 A | 2/1954 | Lowe | |
| 4,727,163 A | 2/1988 | Bellis | |
| 5,023,349 A | 6/1991 | Bhatia | |
| 5,326,887 A | 7/1994 | DiCosimo et al. | |
| 5,342,969 A | 8/1994 | Ford et al. | |
| 5,830,991 A | 11/1998 | Shiiki et al. | |

FOREIGN PATENT DOCUMENTS

| | | |
|---|---|---|
| EP | 0 789023 | 8/1997 |
| FR | 2 692263 | 12/1993 |
| JP | 09-328481 | 12/1997 |
| JP | 2000-119269 | 4/2000 |
| WO | WO 9215572 | 9/1992 |

*Primary Examiner*—Bernard Dentz
(74) *Attorney, Agent, or Firm*—Dinsmore & Shohl LLP

(57) ABSTRACT

The present invention provides a process for production of a cyclic ester by depolymerization of an aliphatic polyester. In the process, a mixture containing the aliphatic polyester and a specific polyalkylene glycol ether, which has a boiling point of 230–450° C. and a molecular weight of 150–450, is heated under normal or reduced pressure to a temperature at which depolymerization of the aliphatic polyester takes place. Then, a substantially homogeneous solution phase, consisting of the melt phase of the aliphatic polyester and the liquid phase of the polyalkylene glycol ether, is formed. Heating of the solution phase is continued to form the cyclic ester by depolymerization and distil out the cyclic ester together with the polyalkylene glycol ether, and then the cyclic ester is recovered from the distillate. The present invention also provides a process for purification of a crude cyclic ester by use of the specific polyalkylene glycol ether described above.

30 Claims, No Drawings

PROCESS FOR THE PREPARATION OF CYCLIC ESTERS AND METHOD FOR PURIFICATION OF THE SAME

This application is a 371 of PCT/JP01/06816 filed Aug. 8, 2001.

TECHNICAL FIELD

The present invention relates to a process for preparing a cyclic ester by depolymerizing an aliphatic polyester. More specifically, the present invention relates to a process for preparing a cyclic ester, such as glycolide, lactide or a lactone, by depolymerizing an aliphatic polyester including from low-molecular-weight material such as oligomer to high-molecular-weight material. Further, the present invention relates to a process for purifying crude cyclic ester.

A cyclic ester obtained by the preparation process and purification process according to the present invention is useful as monomer for ring-opening polymerization. More specifically, a cyclic ester obtained by the production process of the present invention can be polymerized alone through ring opening or copolymerized with another comonomer toproduceapolymer, e.g., polyglycolide (i.e., polyglycolic acid), polylactide (i.e., polylactic acid), a polylactone or a variety of copolymers. These aliphatic polyesters are useful as biodegradable polymeric material, medical polymeric material, etc.

Further, the production process of a cyclic ester according to the present invention is useful not only as production process of a cyclic ester by way of a low-molecular-weight aliphatic polyester, such as an α-hydroxycarboxylic acid oligomer, but as recycling process of product wastes, mold wastes or the likes of high-molecular-weight aliphatic polyester by converting them into a monomeric cyclic ester.

BACKGROUND ART

Aliphatic polyesters, such as polyglycolic acid and polylactic acid, are hydrolyzed in organisms, or degraded in the natural environment through microbial metabolism to produce water and carbon dioxide. Aliphatic polyesters have thus attracted attention as biodegradable polymeric materials, which may replace medical materials or commodity resins.

An aliphatic polyester may be obtained via polycondensation of an α-hydroxycarboxylic acid, such as glycolic acid or lactic acid, but this process is difficult to produce a high-molecular-weight polymer. Therefore, a high-molecular-weight aliphatic polyester for use in molding etc. is generally synthesized via ring-opening (co) polymerization of a cyclic ester, such as glycolide, lactide or a lactone.

Specifically, for instance, polyglycolic acid may be synthesized by dehydrating polycondensation of glycolic acid (i.e., α-hydroxyacetic acid) according to the following Equation [I]:

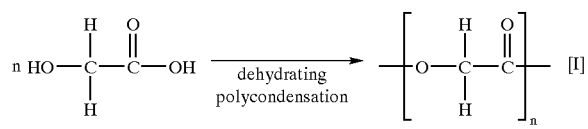

However, this polycondensation process using glycolic acid as starting material is difficult to produce high-molecular-weight polyglycolic acid. Therefore, glycolide, whose structure is a bimolecular cyclic ester of glycolic acid (may be referred to as "dimeric cyclic ester" below), is polymerized in a ring-opening mode in the presence of a catalyst, such as tin octanoate, according to the following Equation [II] to synthesize high-molecular-weight polyglycolic acid (or polyglycolide):

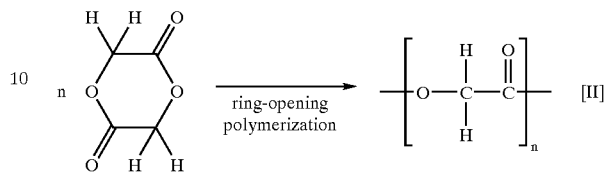

A large scale industrial production of an aliphatic polyester from a cyclic ester, such as glycolide, as starting material essentially requires an efficient and economical supply of a highly pure cyclic ester. However, it has been difficult to synthesize a cyclic ester efficiently and economically. For instance, glycolide is a dimeric cyclic ester whose structure is expressed as one formed by elimination of two molecules of water from two molecules of glycolic acid, but simple esterification of glycolic acid molecules cannot generally produce glycolide, a dimeric cyclic ester but a low-molecular-weight material, such as oligomer. Accordingly, other processes are adopted including, for example, a process where α-hydroxycarboxylic acid oligomer is synthesized and then the oligomer is depolymerized to produce a dimeric cyclic ester.

The conventional technology for production of a dimeric cyclic ester, such as glycolide, is exemplified by the following processes.

U.S. Pat. No. 2,668,162 discloses a process in which a glycolic acid oligomer is ground to powder and the powder is heated at 270–285° C. under an ultra-high vacuum of 12–15 Torr (1.6–2.0 kPa) while feeding the powder to a reaction vessel by extreme bits (about 20 g/hr) to depolymerize it, and resulting vapor containing glycolide produced is collected in a trap. Although this process is feasible on a small scale, it is difficult to enlarge the scale. Therefore, the process is unfit for mass production. In addition, according to this process, the oligomer remains in the reaction vessel as an excessive residue in the form of tar upon the heating, and so the process suffers from low yield and troublesome removal of the residue. Further, in this process, there is a possibility that a glycolide having high melting point may deposit together with byproducts on the inner wall surface of a recovery line to block the line. It is also difficult to recover the accumulated product in the line.

U.S. Pat. No. 4,727,163 discloses a process in which a polyether with a high heat stability is used as a substrate, a block copolymer of the polyether with a small amount of glycolic acid is formed, and the copolymer is then heated and depolymerized to obtain glycolide. However, the block copolymerization process suffers from many steps, complicated operations and high production cost. Further, according to this process, there is a possibility that a glycolide having high melting point may deposit together with byproducts on the inner wall surface of a recovery line to block the line. It is also difficult to recover the accumulated product in the line.

U.S. Pat. Nos. 4,835,293 and 5,023,349 disclose a process in which an α-hydroxycarboxylic acid oligomer is heated into a melt, an inert gas, e.g., nitrogen gas is blown onto the surface of the melt, and a cyclic ester generated and vaporized from the surface of the melt is carried with the gas stream to collect it. According to this process, the rate of formation of the cyclic ester is low, a large volume of the inert gas to be blown requires preheating it and so forth, resulting in a high production cost. In addition, tar formation progresses in the interior of the oligomer melt during the heating, and excessive tar remains as a residue in a reaction vessel. Therefore, this process suffers from low yield and troublesome removal of the residue.

French Patent No. 2,692,263-A1 discloses a process in which an oligomer of α-hydroxycarboxylic acid, its ester or its salt is added to a solvent where a catalyst has been added, and the mixture is stirred under heating to decompose it catalytically. According to this process, the reaction is conducted under normal or elevated pressure using a solvent suitable to carry the cyclic ester in a gaseous state, and the gas phase is then condensed to recover the cyclic ester and the solvent. The publication demonstrates an example where a lactic acid oligomer is used with dodecane as solvent (with boiling point around 214° C.). The present inventors traced the example using a glycolic acid oligomer and dodecane under similar conditions, and it was revealed that tar formation took place as soon as depolymerization started and glycolide formation was stopped at the point when a minute amount of glycolide was formed. What was worse, the reaction residue was so viscous as to require much effort for cleaning it off.

U.S. Pat. No. 5,326,887 and WO92/15572A1 disclose a process in which a glycolic acid oligomer is heated and depolymerized over a fixed bed catalyst to produce glycolide. According to this process, however, a considerable amount of tar is formed upon the heating and remains as a residue. Therefore, the process suffers from low yield and troublesome cleaning on the fixed bed.

In Japanese Patent Laid-Open No. 9-328481 (corresponding to U.S. Pat. No. 5,830,991), the inventors common to the present invention presented a process in which a polar organic solvent with a high boiling point is used in production of a dimeric cyclic ester derived from an α-hydroxycarboxylic acid via depolymerization of an α-hydroxycarboxylic acid oligomer. This process comprises heating a mixture containing the α-hydroxycarboxylic acid oligomer and the high boiling polar organic solvent to a temperature at which depolymerization of the oligomer takes place, in order to form a substantially homogeneous solution phase, further continuing the heating at the temperature to form the dimeric cyclic ester, distilling out the formed ester together with the high boiling polar organic solvent, and recovering the dimeric cyclic ester from the distillate. According to this process, a dimeric cyclic ester can be obtained from an α-hydroxycarboxylic acid oligomer in a high yield while conversion of the oligomer into tar is prevented.

In this document, many polar solvents within the range of 230–450° C. of boiling point are exemplified as high boiling polar organic solvent. Solvents used in the examples are di(2-methoxyethyl) phthalate, diethylene glycol dibenzoate, benzyl butyl phthalate, dibutyl phthalate and tricresyl phosphate, which are all aromatic ester compounds. When the inventors studied depolymerization in more detail using these aromatic ester compounds as high boiling polar organic solvent, prolonged heating of those compounds at the temperature when depolymerization of an α-hydroxycarboxylic acid oligomer takes place was found to tend to thermally deteriorate the aromatic ester compounds. Thermal deterioration of the aromatic ester compounds requires conduction of a purification step, if they are to be used again. In addition, an amount corresponding to deterioration of such an aromatic ester compound must be added again in the reaction of depolymerization. Consequently, it is difficult to reduce further the production cost of a dimeric cyclic ester.

Further, few depolymerization processes using an aliphatic polyester, such as poly(α-hydroxycarboxylic acid) with a high molecular weight, have been described, since conventional processes use mainly α-hydroxycarboxylic acid oligomers as starting material. Japanese Patent Laid-Open No. 12-119269 describes a process in which polyglycolic acid is depolymerized in the solid phase within the temperature range not lower than 200° C. and below 245° C. to produce glycolide. However, this process is not necessarily suitable for efficient mass production of glycolide on an industrial scale. Also, unless heating temperature is controlled rigorously in this process, polyglycolic acid is liable to degenerate into tar.

Mass production of a high-molecular-weight aliphatic polyester, such as poly(α-hydroxycarboxylic acid), will force recycling of product wastes into a major subject. Recycling of mold wastes generated during molding of an aliphatic polyester will be another subject. It will facilitate the recycling to depolymerize a high-molecular-weight aliphatic polyester to the cyclic ester efficiently and economically.

DISCLOSURE OF THE INVENTION

It is an object of the present invention to provide a process for preparing a cyclic ester by economically and efficiently depolymerizing an aliphatic polyester including from low-molecular-weight material such as oligomer to high-molecular-weight material.

More specifically, it is an object of the present invention to provide a process for preparing a cyclic ester from an aliphatic polyester by improving the process in which an α-hydroxycarboxylic acid oligomer is depolymerized in the presence of a high boiling polar organic solvent, wherein thermal deterioration of the polar organic solvent is controlled during the depolymerization.

It is another object of the present invention to provide a process for economically and efficiently purifying a crude cyclic ester.

The inventors have made every effort to attain the objects described above. As a result, selective use of particular polyalkylene glycol ethers, which are not specifically described as high boiling polar organic solvent in Japanese Patent Laid-Open No. 9-328,481 (or U.S. Pat. No. 5,830, 991) aforementioned, has been found to depolymerize an aliphatic polyester without thermal deterioration of the polar organic solvent to produce the cyclic ester.

More specifically, the process can produce the cyclic ester efficiently and economically without thermal deterioration of a particular polyalkylene glycol ether, by heating a mixture containing the aliphatic polyester and the polyalkylene glycol ether under normal or reduced pressure to a temperature at which depolymerization of the aliphatic polyester takes place, in order to form a substantially homogeneous solution phase consisting of the melt phase of the aliphatic polyester and the liquid phase of the polyalkylene glycol ether, and continuing to heat the solution phase to make the depolymerization proceed. The aliphatic polyester may be either homopolymer or copolymer if it is an aliphatic polyester having repeat units which can form a cyclic ester by depolymerization.

According to this process, the cyclic ester formed by depolymerization is distilled off together with the polyalkylene glycol ether and both compounds are separated into distinct liquid phases to recover the cyclic ester phase, while the polyalkylene glycol ether phase without thermal deterioration may be circulated to the reaction system of depolymerization for its reuse. The polyalkylene glycol ether phase may be used in another reaction system of depolymerization. Polyalkylene glycol ether remaining in the reaction system of depolymerization may also be used again.

Further, this process may use not only low-molecular-weight materials, such as an α-hydroxycarboxylic acid oligomer, but high-molecular-weight aliphatic polyesters including product wastes, mold wastes or the likes as starting material to produce a cyclic ester by depolymerization. When a high-molecular-weight aliphatic polyester is poorly soluble in the polyalkylene glycol ether, any suitable solubilizing agent may be used in combination and/or the reaction of depolymerization may be conducted under reduced pressure or under any suitable conditions.

Still further, this process may be applied to purify a crude cyclic ester.

The process according to the present invention may reduce the production cost considerably and contribute greatly to an industrial mass production of a cyclic ester, since no deterioration of a polar organic solvent used in depolymerization is induced and the polar organic solvent once used may be used again. In addition, the process according to the present invention may recycle high-molecular-weight aliphatic polyesters by converting them to the cyclic esters. The present invention has been completed based on the above findings.

Thus, the present invention provides a process for production of a cyclic ester by depolymerization of an aliphatic polyester, characterized in that the process comprises the steps of (I) heating a mixture containing the aliphatic polyester (A) and a polyalkylene glycol ether (B), which is represented by the following formula (1)

$$X^1-O+R^1-O+_p Y \tag{1}$$

where $R^1$ is a methylene group, or a straight-chain or branched-chain alkylene group with 2–8 carbons, $X^1$ is a hydrocarbon group, Y is an alkyl or aryl group with 2–20 carbons, p is an integer not smaller than 1 and when p is 2 or greater, a plurality of $R^1$ groups may be identical or different, and has a boiling point of 230–450° C. and a molecular weight of 150–450, under normal or reduced pressure to a temperature at which depolymerization of the aliphatic polyester (A) takes place, (II) forming a substantially homogeneous solution phase consisting of the melt phase of the aliphatic polyester (A) and the liquid phase of the polyalkylene glycol ether (B), (III) continuing to heat the solution phase to form the cyclic ester by depolymerization and distil off the cyclic ester together with the polyalkylene glycol ether (B), and (IV) recovering the cyclic ester from the distillate.

Further, the present invention provides a process for purification of a crude cyclic ester, characterized in that the process comprises the steps of heating a mixture containing the crude cyclic ester (A') and a polyalkylene glycol ether (B), which is represented by the following formula (1)

$$X^1-O+R^1-O+_p Y \tag{1}$$

where $R^1$ is a methylene group, or a straight-chain or branched-chain alkylene group with 2–8 carbons, $X^1$ is a hydrocarbon group, Y is an alkyl or aryl group with 2–20 carbons, p is an integer not smaller than 1 and when p is 2 or greater, a plurality of $R^1$ groups may be identical or different, and has a boiling point of 230–450° C. and a molecular weight of 150–450, under normal or reduced pressure in order to form a substantially homogeneous solution phase without phase separation of the components; continuing to heat the solution phase to distil off the cyclic ester (A) together with the polyalkylene glycol ether (B); and recovering the cyclic ester (A) from the distillate.

BEST MODE FOR CARRYING OUT THE INVENTION

1. Cyclic Esters and Aliphatic Polyesters (A)

The process for production of a cyclic ester according to the present invention may be applied to produce an intermolecular cyclic ester of two molecules of an α-hydroxycarboxylic acid, such as glycolic acid, lactic acid, α-hydroxybutyric acid or α-hydroxyvaleric acid, in other words, a dimeric cyclic ester. For example, the dimeric cyclic ester of glycolic acid is glycolide, and the dimeric cyclic ester of lactic acid is lactide (D-lactide and/or L-lactide).

The process for production of a cyclic ester according to the present invention may also be applied to produce a lactone, such as β-propiolactone, β-butyrolactone, pivalolactone, γ-butyrolactone, δ-valerolactone, β-methyl-δ-valerolactone, or ε-caprolactone. Such a lactone is a cyclic ester which is polymerized through ring opening to provide an open-ring polymer having repeat units (—O—R—CO—) (R is an alkylene group) derived from "hydroxycarboxylic acid".

The aliphatic polyester used as starting material according to the present invention may be a (co)polymer having repeat units which can form a cyclic ester by depolymerization. Such an aliphatic polyester may be produced by (co)polymerizing a cyclic ester, such as glycolide, lactide or a lactone, as monomer through ring opening. Such an aliphatic polyester may also be produced by polycondensation of α-hydroxycarboxylic acid, such as glycolic acid or lactic acid, its alkyl ester or its salt.

Examples of the aliphatic polyester used in the present invention include a poly(α-hydroxycarboxylic acid), such as polyglycolic acid (including polyglycolide) or polylactic acid (including polylactide); a polylactone, such as poly(ε-caprolactone); and a copolyester, such as an open-ring copolymer of plural cyclic esters, a copolymer of a cyclic ester with a comonomer of another type, a copolymer of plural α-hydroxycarboxylic acids or a copolymer of an α-hydroxycarboxylic acid with a comonomer of another type.

In the present invention, any aliphatic polyester having repeat units (—O—R—CO—) derived from "hydroxycarboxylic acid", including a poly(α-hydroxycarboxylic acid) and also a polylactone, will be referred to as polyhydroxycarboxylic acid. In addition, polyglycolic acid, polylactic acid or the like will be referred to as poly(α-hydroxycarboxylic acid), whether it may be produced by polycondensation of α-hydroxycarboxylic acid or by ring opening of a dimeric cyclic ester.

In the present invention, an aliphatic polyester is defined to include from a low-molecular-weight material, such as an oligomer, to a high-molecular-weight material. A low-molecular-weight aliphatic polyester, such as an oligomer, cannot be always distinguished definitely from a high-molecular-weight aliphatic polyester. In the present invention, however, a low-molecular-weight material with a weight-average molecular weight less than 10,000 and mostly less than 5,000 is defined as oligomer or low-molecular-weight aliphatic polyester, such as oligomer. Degree of polymerization for the oligomer, i.e., the number of repeat units (—O—R—CO—) derived from "hydroxycarboxylic acid" is typically 2 or more, and preferably 5 or more.

A high-molecular-weight aliphatic polyester typically has a weight-average molecular weight equal to 10,000 or higher, preferably from 10,000 to 1,000,000, and more preferably from 20,000 to 800,000. The weight-average molecular weight is determined through measurement by gel permeation chromatography (GPC). As for poly(α-hydroxycarboxylic acid), such as polyglycolic acid (i.e., polyglycolide), for example, GPC measurement using hexafluoroisopropanol (HFIP) as solvent determines its weight-average molecular weight as an equivalent to the standard poly(methyl methacrylate) (PMMA).

The aliphatic polyester used is generally a polyhydroxycarboxylic acid with repeat units derived from a hydroxycarboxylic acid. Of those polyhydroxycarboxylic acids, a poly(α-hydroxycarboxylic acid), such as polyglycolic acid (i.e., polyglycolide) or polylactic acid (i.e., polylactide), is more preferable, and polyglycolic acid is most preferable. The aliphatic polyester may be a copolymer, which preferably contains 50% or more by weight of repeat units derived from α-hydroxycarboxylic acid, such as glycolic acid or lactic acid.

The different aliphatic polyesters may be synthesized according to the conventional processes, respectively. For instance, a low-molecular-weight material, such as an α-hydroxycarboxylic acid oligomer, may be produced through polycondensation of α-hydroxycarboxylic acid, or an alkyl ester (of an alkyl group typically with 1–4 carbons) or a salt thereof, if necessary, in the presence of a catalyst.

More specifically, glycolic acid oligomer, for example, used as starting material for glycolide, may be synthesized by heating glycolic acid, or an ester or a salt thereof at a temperature of 100–250° C., preferably 140–230° C. under reduced or elevated pressure in the presence of an optional condensation or transesterification catalyst in order to conduct a condensation or transesterification reaction until low-molecular-weight compounds such as water and alcohol substantially has ceased to be distilled out. After completion of the condensation or transesterification reaction, the oligomer formed may be used directly as starting material for the preparation process of the present invention. The oligomer thus obtained may also be taken out of the reaction system and washed with a non-solvent such as benzene or toluene to remove an unreacted material and the catalyst before its use. The oligomer may be either cyclic or linear in structure. Any other α-hydroxycarboxylic acid oligomer may be synthesized in a similar process.

The oligomer may be low in degree of polymerization, but typically has a melting point (Tm) of at least 140° C., preferably at least 160° C., more preferably at least 180° C. from the viewpoint of yield of the cyclic ester, such as glycolide, formed by the depolymerization. Here, Tm refers to a melting point detected at the time the oligomer is heated at a rate of 10° C./min in an inert gas atmosphere by means of a differential scanning calorimeter (DSC).

The high-molecular-weight aliphatic polyester may be synthesized from glycolide, lactide or a lactone by ring-opening (co)polymerization. In addition, product wastes after use, mold wastes and the likes may be used suitably as high-molecular-weight aliphatic polyester and thereby recycled. The high-molecular-weight aliphatic polyester may be of any shape, for example, in the form of sheets (or plates), film, fibers, spheres, cylinders, or rods. These shapes of polyester may be preferably converted into granules, powders, fibers, etc., before depolymerization to increase the efficiency of the reaction. For that purpose, they may be crushed, ground or melted to make granules or powders or they may be melted and drawn to make fibers before feeding them for depolymerization.

According to the present invention, the aliphatic polyester may be placed into a reactor in bulk before the reaction, or added continuously, intermittently or in combination during the reaction. However, the aliphatic polyester in the reactor is required to be in a substantially homogeneous phase (in a solution state) formed together with the polar organic solvent during the depolymerization, as described later. A spare reactor may be provided and used so that the melt phase of the aliphatic polyester and the liquid phase of the polar organic solvent may form together a more homogeneous phase there, before the homogeneous phase formed there is introduced into the reactor for depolymerization. In addition, a solubilizing agent, as described later, may be combined with the polar organic solvent to form a substantially homogeneous phase.

2. Polyalkylene Glycol Ethers (B)

A polar organic solvent used in a process for production of a cyclic ester or a process for purification of a crude cyclic ester according to the present invention is a polyalkylene glycol ether (B) which is represented by the following formula (1)

where $R^1$ is a methylene group, or a straight-chain or branched-chain alkylene group with 2–8 carbons, $X^1$ is a hydrocarbon group, Y is an alkyl or aryl group with 2–20 carbons, p is an integer not smaller than 1 and when p is 2 or greater, a plurality of $R^1$ groups may be identical or different, and has a boiling point of 230–450° C. and a molecular weight of 150–450.

Such a polyalkylene glycol ether (B) is used as polar organic solvent for depolymerization of the aliphatic polyester and for removal of the cyclic ester formed, such as glycolide, from the reaction system.

The polyalkylene glycol ether (B) used in the present invention is one having an alkyl or aryl group with two or more carbons at at least one terminal ether group.

The polyalkylene glycol ether (B) has a boiling point of 230–450° C. If the boiling point of the polyalkylene glycol ether (B) is too low, the temperature for depolymerization cannot be raised sufficiently, leading to a lower rate of formation of the cyclic ester, such as glycolide. On the contrary, if the boiling point of the polyalkylene glycol ether (B) is too high, the polyalkylene glycol ether is difficult to distil off and thereby difficult to distil off together with the cyclic ester formed by depolymerization. The polyalkylene glycol ether (B) has preferably a boiling point of 235–450° C., more preferably 240–430° C., and most preferably 250–420° C.

The polyalkylene glycol ether (B) has a molecular weight of 150–450. When the molecular weight of the polyalkylene glycol ether (B) is either too low or too high, it is difficult to distil off together with the cyclic ester, such as glycolide. The polyalkylene glycol ether (B) has preferably a molecular weight of 180–420, and more preferably 200–400.

As described above, the polyalkylene glycol ether (B) used in the present invention has an alkyl or aryl group with two or more carbons as at least one end group (Y). In the case where ether groups having an alkyl group with one carbon are present at both ends, the carbon number of $R^1$ needs to be increased so that the polyalkylene glycol ether may become a high boiling solvent suitable to distil off together with glycolide. Such a polyalkylene glycol ether is synthesized with a resultant broad distribution of p, i.e., repeat number of ($-R^1-O-$) units, and so it is necessary to distil the synthesized material for purification, which may result in more complex steps and a lower yield. Consequently, such a polyalkylene glycol ether is not suitable for industrial-scale practice.

In Japanese Patent Laid-Open No. 9-328481 (U.S. Pat. No. 5,830,991), hexaethylene glycol dimethyl ether (molecular weight: 310) is described as an example of the polar organic solvent, but in fact it is necessary to separate it from polyethylene glycol dimethyl ethers with a corresponding range of molecular weight for purification. However, a commercially available grade of polyethylene glycol dimethyl ethers (average molecular weight: about 250), which is suitable for the raw material of hexaethylene glycol dimethyl ether, has a broad distribution of polymerization degree in the range of 4–8, even if only main components are concerned, and contains only about 20–30 wt % of the object compound with 6 of polymerization degree based on the weight of the raw material.

In Formula (1) described above, $X^1$ is a hydrocarbon group, for example, an alkyl group, an aryl group and so forth.

In the case where ether groups ($X^1$ and Y) at both ends of the polyalkylene glycol ether contain more than 21 carbons together, the polarity of this compound is decreased, and thus it becomes difficult for the compound to form a homogeneous melt phase with the aliphatic polyester during depolymerization. If the polar organic solvent is a polyalkylene glycol derivative, which does not bear a terminal ether group but a terminal hydroxyl group and/or a terminal ester group, the solvent is liable to undergo thermal degradation during depolymerization, resulting in a higher production cost.

The polyalkylene glycol ether (B) desirably has alkyl groups within ether groups ($X^1$ and Y) at both ends, and the total number of carbons contained together in the alkyl groups within ether groups at both ends is preferably 3–21, and more preferably 6–20. Examples of the alkyl groups include propyl, butyl, pentyl, hexyl, heptyl, octyl, nonyl, decyl and lauryl groups. These alkyl groups may be linear or branched. If the total number of carbons contained together in alkyl groups is more than 21 in a polyalkylene glycol ether, its molecular weight tends to be over 450, making it difficult to distil it off together with the cyclic ester, such as glycolide during depolymerization.

A polyalkylene glycol dialkyl ether is preferably a polyethylene glycol dialkyl ether where diethylene glycol dialkyl ether, triethylene glycol dialkyl ether and tetraethylene glycol dialkyl ether are more preferable.

The alkyl groups within ether groups at both ends of the polyalkylene glycol ether (B) may have the same number of carbons, for example, dibutyl, dihexyl or dioctyl, but are not necessarily have the same number of carbons. They may be a combination of different alkyl groups, e.g., propyl and lauryl groups, hexyl and heptyl groups, or butyl and octyl groups.

In the case where Y is an aryl group in Formula (1), examples thereof include phenyl, naphthyl, substituted phenyl and substituted naphthyl groups. The substituents are preferably alkyl groups, alkoxyl groups and halogen atoms (chlorine, bromine, iodine, etc.). A substituted phenyl group has typically 1–5 substituents and preferably 1–3 substituents. When there are plural substituents, they may be identical or different. Substituents play a role in adjusting the boiling point and polarity of the polyalkylene glycol ether (B).

The property of the polyalkylene glycol ether also varies with p, i.e., repeat number of alkyleneoxy units ($-R^1-O-$) in Formula (1). The polyalkylene glycol ether (B) used in the present invention has the repeat number p of 2–8, and preferably 2–5. As the repeat number p is larger, the distribution of polymerization degree in its synthesis by polyaddition reaction may be broader, making it more difficult to isolate a polyalkylene glycol ether with the same repeat number of units. In particular, the repeat number of units p more than 8 corresponds to a high-molecular-weight polyalkylene glycol ether which is difficult to distil and isolate, thus reducing the yield.

The alkyleneoxy unit ($-R^1-O-$) is not limited in particular, provided that $R^1$ is a methylene group, or a straight-chain or branched-chain alkylene group with 2–8 carbons. Examples include polyethylene glycol ether composed of ethyleneoxy units with $R^1$ having 2 carbons, polypropylene glycol ether composed of propyleneoxy units with $R^1$ having 3 carbons and polybutylene glycol ether composed of butyleneoxy units with $R^1$ having 4 carbons. Of these, polyethylene glycol ether is particularly preferable, since the starting material is easily available and it is easy to synthesize.

In the case where the repeat number p of alkyleneoxy units ($-R^1-O-$) is 2 or more, plural $R^1$s may be identical or different. An example with plural different $R^1$s is a polyalkylene glycol ether containing ethyleneoxy units and propyleneoxy units, which is formed by mixing ethylene oxide and propylene oxide to make them react with each other, but not limited thereto.

Examples of the polyalkylene glycol ether (B) include polyethylene glycol dialkyl ether, such as diethylene glycol dibutyl ether, diethylene glycol dihexyl ether, diethylene glycol dioctyl ether, triethylene glycol dibutyl ether, triethylene glycol dihexyl ether, triethylene glycol dioctyl ether, tetraethylene glycol dibutyl ether, tetraethylene glycol dihexyl ether, tetraethylene glycol dioctyl ether, diethylene glycol butyl hexyl ether, diethylene glycol butyl octyl ether, diethylene glycol hexyl octyl ether, triethylene glycol butyl hexyl ether, triethylene glycol butyl octyl ether, triethylene glycol hexyl octyl ether, tetraethylene glycol butyl hexyl ether, tetraethylene glycol butyl octyl ether or tetraethylene glycol hexyl octyl ether; polyalkylene glycol dialkyl ether, such as polypropylene glycol dialkyl ether or polybutylene glycol dialkyl ether, which contains propyleneoxy or butyleneoxy units in stead of ethyleneoxy units within the polyethylene glycol dialkyl ether described above; polyethylene glycol alkyl aryl ether, such as diethylene glycol butyl phenyl ether, diethylene glycol hexyl phenyl ether, diethylene glycol octyl phenyl ether, triethylene glycol butyl phenyl ether, triethylene glycol hexyl phenyl ether, triethylene glycol octyl phenyl ether, tetraethylene glycol butyl phenyl ether, tetraethylene glycol hexyl phenyl ether, tetraethylene glycol octyl phenyl ether, or polyethylene glycol alkyl aryl ether which has substituted any of alkyl groups, alkoxyl groups, halogen atoms, etc. for at least one hydrogen atom of the phenyl group within the compounds listed just above; polyalkylene glycol alkyl aryl ether, such as polypropylene glycol alkyl aryl ether or polybutylene glycol alkyl aryl ether, which contains propyleneoxy or butyleneoxy units in stead of ethyleneoxy units within the polyethylene glycol alkyl aryl ether described above; polyethylene glycol diaryl ether, such as diethylene glycol diphenyl ether, triethylene glycol diphenyl ether, tetraethylene glycol diphenyl ether, or a compound which has substituted any of alkyl groups, alkoxyl groups, halogen atoms, etc. for at least one hydrogen atom of the phenyl groups within the compounds listed just above; polyalkylene glycol diaryl ether, such as polypropylene glycol diaryl ether or polybutylene glycol diaryl ether, which contains propyleneoxy or butyleneoxy units in stead of ethyleneoxy units within the polyethylene glycol diaryl ether described above; and the likes.

The polyalkylene glycol ether (B) used in the present invention preferably has the following features.

The percentage of the amount of the polyalkylene glycol ether (B) remaining in the reaction solution after depolymerization plus the amount thereof recovered from the distillate to the feed amount thereof, that is, the recovery rate is preferably 85% or more, more preferably 90% or more, and still more preferably 95% or more. If the recovery rate of the polyalkylene glycol ether (B) is too low, it is difficult to reduce the production cost. In this case, purification of the polyalkylene glycol ether containing more impurities is more costly.

The solubility of a cyclic ester, such as glycolide, in the polyalkylene glycol ether (B) used in the present invention is preferably at least 0.1% at 25° C. Inmost cases, a polyalkylene glycol ether (B) is preferable where the cyclic ester is soluble in the range of 0.1–10%. Herein, the solubility of a cyclic ester at 25° C. is expressed as a percentage of the weight B (g) of the cyclic ester to the volume A (ml) of the polyalkylene glycol ether (B) when the cyclic ester, such as glycolide, has been dissolved to the saturation in the polyalkylene glycol ether (B) at 25° C. Accordingly, the solubility is expressed by the following equation:

Solubility(%)=(B/A)×100

If the solubility is too low, the cyclic ester, such as glycolide, distilled off together with the polyalkylene glycol ether (B) deposits and tends to block the recovery line and cause some other troubles, and so it is not a favorable solvent. If the solubility is too high, on the contrary, recovery of the cyclic ester from the co-distillate obtained by depolymerization requires an extra proper procedure, for example, cooling it down to 0° C. or lower, or addition of a non-solvent therein, to isolate the cyclic ester. It requires a great amount of energy to cool it to a low temperature on an industrial scale. Addition of the non-solvent requires separation of the non-solvent from the polyalkylene glycol ether (B) to be recovered and used again, which necessitates extra processing steps and equipment, making the process unfavorable for industrial practice.

The polyalkylene glycol ether (B) may be prepared, for example, by addition or polyaddition of an alkylene oxide to an alcohol to produce an alkylene glycol monoether or a polyalkylene glycol monoether, followed by etherification of the hydroxyl end group of the monoether intermediate. Processes of etherification are known and not limited in particular. Examples of the processes generally include a process of reacting a polyalkylene glycol monoether with an alkyl halide in the presence of any of metallic sodium, sodium hydride, sodium hydroxide, etc.; a process following the above process under the co-existence of sodium iodide; a process following the above process again except for the use of a sulfonated alcohol as alkylating agent, which is prepared from the alcohol and a sulfonyl chloride (e.g., tosyl chloride, mesyl chloride, etc.) in the presence of a base, in stead of the alkyl halide (i.e., an alkylating agent); and the likes.

3. Solubilizing Agents (C)

According to the present invention, a solubilizing agent may be used to improve the dissolution properties (solubility and/or rate of dissolution) of the aliphatic polyester, such as glycolic acid oligomer or polyglycolide, for the polyalkylene glycol ether (B).

The solubilizing agent used in the present invention preferably satisfies at least one of the following requirements:

(i) it should be a non-basic compound, since a basic compound, such as an amine, pyridine or quinoline, may unfavorably react with the aliphatic polyester and/or the cyclic ester formed;

(ii) it should be miscible with or soluble in the polyalkylene glycol ether (B), whether it may be either liquid or solid at the ambient temperature;

(iii) it should have a boiling point of at least 180° C., preferably at least 200° C., more preferably at least 230° C., and most preferably at least 250° C.: in particular, when it has a higher boiling point than that of a polyalkylene glycol ether (B) used in depolymerization, preferably it is not distilled ever or distilled minimally with the cyclic ester, such as glycolide, and the polyalkylene glycol ether (B) while the cyclic ester is distilled off; in most cases, when it has a boiling point of at least 450° C., a good result may be obtained; however, alcohols and the likes are exceptions since they may be used suitably as solubilizing agent, whether they may have a lower boiling point than that of the polyalkylene glycol ether (B) used in depolymerization;

(iv) it should have a functional group such as, for example, an OH, COOH or CONH group; and (v) it should have a higher affinity for the aliphatic polyester (A) than for the polyalkylene glycol ether (B): affinity of a solubilizing agent for the aliphatic polyester (A) may be evaluated according to a procedure comprising the steps of a) heating a mixture of the aliphatic polyester (A) and the polyalkylene glycol ether (B) to 230–280° C. to form a homogeneous solution phase, b) adding further the aliphatic polyester (A) thereto to maximize its concentration until the homogeneous solution phase cannot be maintained any longer, and c) adding the solubilizing thereto and seeing by macroscopic observation if a homogeneous solution phase may be formed again.

Examples of the solubilizing agent used in the present invention include monohydric alcohol or a polyhydric alcohol with more than one hydroxyl groups (including a partial ester or ether thereof), a phenol, aliphatic monocarboxylic acid or an aliphatic polycarboxylic acid with more than one carboxyl groups, an aliphatic amide, which is produced from an aliphatic carboxylic acid and an amine, an aliphatic imide, a polyalkylene glycol ether with molecular weight more than 450, and the likes. These compounds may be used alone or in combination of two or more compounds.

Of these compounds, monohydric alcohol or a polyhydric alcohol is especially efficient as solubilizing agent. The monohydric or polyhydric alcohol has a boiling point of at least 180° C., preferably at least 200° C., more preferably at least 230° C., and most preferably at least 250° C. More specifically, the alcohols include aliphatic alcohols, such as decanol, tridecanol, decanediol, ethylene glycol, propylene glycol, and glycerol; aromatic alcohols, such as cresols, chlorophenols, and naphthylalcohols; polyalkylene glycols; polyalkylene glycol monoethers; and the likes.

The polyalkylene glycol is preferably one represented by the following formula (2)

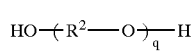

(2)

where $R^2$ is a methylene group, or a straight-chain or branched-chain alkylene group with 2–8 carbons, q is an integer not smaller than 1 and when q is 2 or greater, a plurality of $R^2$ groups may be identical or different. Examples of the polyalkylene glycol include polyethylene glycol, polypropylene glycol and polybutylene glycol. These compounds may be used alone or in combination of two or more compounds.

The polyalkylene glycol monoether is preferably one represented by the following formula (3)

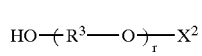

(3)

where $R^3$ is a methylene group, or a straight-chain or branched-chain alkylene group with 2–8 carbons, $X^2$ is a hydrocarbon group, r is an integer not smaller than 1 and when r is 2 or greater, a plurality of $R^3$ groups may be identical or different. Examples of the polyalkylene glycol monoether include polyethylene glycol monomethyl ether, polyethylene glycol monoether, such as polyethylene glycol monopropyl ether, polyethylene glycol monobutyl ether, polyethylene glycol monohexyl ether, polyethylene glycol monooctyl ether, polyethylene glycol monodecyl ether, or polyethylene glycol monolauryl ether; and polyalkylene glycol monoether, such as polypropylene glycol monoether or polybutylene glycol monoether, which contains propyleneoxy or butyleneoxy units in stead of ethyleneoxy units within the polyethylene glycol monoether described above. The polyethylene glycol monoether preferably has the alkyl group with 1–18 carbons and more preferably with 6–18 carbons within the terminal ether group. These compounds may be used alone or in combination of two or more compounds.

When a polyalkylene glycol or a polyalkylene glycol monoether is used as solubilizing agent, these compounds are hardly distilled off due to their high boiling points. In addition, since the polyalkylene glycol or the polyalkylene glycol monoether dissolves the aliphatic polyester to a great extent, the use of these as solubilizing agent makes the depolymerization of the aliphatic polyester proceed rapidly. Furthermore, the use of the polyalkylene glycol monoether as solubilizing agent is especially effective in cleaning the tank wall (the inner wall of the reactor).

In the present invention, a polyalkylene glycol ether, which has a higher affinity for the aliphatic polyester, a higher molecular weight and a higher boiling point, compared with the polyalkylene glycol ether (B) used as polar organic solvent for depolymerization, may be used as solubilizing agent. Examples of the polyalkylene glycol ether suitable as solubilizing agent include polyethylene glycol dimethyl ether #500 (average molecular weight: 500) and polyethylene glycol dimethyl ether #2000 (average molecular weight: 2000). The polyalkylene glycol ether as solubilizing agent has a molecular weight more than 450. If it has a lower molecular weight, it may be distilled off together with the cyclic ester during depolymerization and lose a solubilizing function of keeping the aliphatic polyester soluble in the reaction system for depolymerization.

Although the action of the solubilizing agent is not yet completely clarified, it is considered to be attributable to an effect that it acts on an aliphatic polyester chain at a terminal(s) thereof to change the aliphatic polyester to a more soluble matter, an effect that it acts on the molecular chain of the aliphatic polyester at an intermediate site thereof to cleave the molecular chain thereof, thereby modifying the molecular weight thereof to make it more soluble, an effect that the polarity of the whole solvent system is varied to enhance hydrophilicity, thereby enhancing the solubility of the aliphatic polyester in the solvent, an effect that it disperses and emulsifies the aliphatic polyester or the combined effect thereof.

The solubilizing agent is typically used in a proportion of 0.1–500 parts by weight, and preferably 1–300 parts by weight per 100 parts by weight of the aliphatic polyester. If the proportion of the solubilizing agent is too low, its solubilizing effect is insufficient. If the proportion of the solubilizing agent is too high, recovery of the solubilizing agent is costly and uneconomical.

4. Catalyst (D)

In the preparation process of a cyclic ester according to the present invention, the aliphatic polyester is dissolved in the polyalkylene glycol ether (B), whereby the surface area thereof is extremely widened. Therefore, the generation rate or vaporization rate of the cyclic ester, such as glycolide, by the depolymerization is high. It is generally thus unnecessary to use any catalyst (e.g., a tin or antimony compound) for the depolymerization. In the preparation process of the present invention using the thermally very stable polyalkylene glycol ether (B), use of a catalyst may be rather detrimental. However, it is permissible to use a catalyst so far as no detrimental effect is basically imposed on the "solution-phase depolymerization process" of the present invention.

5. Preparation Process of a Cyclic Ester

The preparation process of a cyclic ester according to the present invention comprises the following steps:

(I) a step of heating a mixture containing an aliphatic polyester (A) and a polyalkylene glycol ether (B), which is represented by the above formula (1) and has a boiling point of 230–450° C. and a molecular weight of 150–450, under normal or reduced pressure to a temperature at which depolymerization of the aliphatic polyester (A) takes place, (II) a step of forming a substantially homogeneous solution phase consisting of the melt phase of the aliphatic polyester (A) and the liquid phase of the polyalkylene glycol ether (B), (III) a step of continuing to heat the solution phase to form the cyclic ester by depolymerization and distil off the cyclic ester together with the polyalkylene glycol ether (B), and (IV) a step of recovering the cyclic ester from the distillate.

The preparation process of a cyclic ester according to the present invention is best characterized by conducting depolymerization of an aliphatic polyester in a solution phase. The depolymerization is usually conducted at a temperature of 200° C. or higher. In the case where a major portion of the aliphatic polyester is insoluble in the solvent and forms a melt phase, the cyclic ester formed is difficult to distil off and the melt phase is liable to form tar. When a major portion of the aliphatic polyester is dissolved and then heated in a solution phase, the generation rate and vaporization rate of the cyclic ester are increased dramatically.

Specifically, in the above step (I), the aliphatic polyester (A) is introduced first into the reactor either in a melt state or in a solid state, optionally after grinding it down to a suitable particle size, and then the polyalkylene glycol ether (B) is added to mix with the polyester. The mixture containing the aliphatic polyester (A) and the polyalkylene glycol ether (B) is typically heated to at least 200° C. to form a substantially homogeneous liquid phase (solution state) where all or a major portion of the aliphatic polyester is dissolved in the polyalkylene glycol ether (B). It is preferable to melt and dissolve the aliphatic polyester under an inert gas atmoshere, such as nitrogen gas. When the aliphatic polyester (A) is not sufficiently soluble in the polyalkylene glycol ether (B) due to high molecular weight or so, the solubilizing agent (C) should be added.

In the above step (II), a homogeneous liquid phase consisting of the aliphatic polyester (A) and the polyalkylene glycol ether (B) is preferably formed, but if the remaining rate of the melt phase of the aliphatic polyester is 0.5 or less, the melt phase of the aliphatic polyester may be present together with the solution. Herein, the "remaining rate of the melt phase" is expressed by b/a, wherein a (ml) designates the melt-phase volume of the aliphatic polyester, which is formed on heating F (g) of the aliphatic polyester added to a solvent substantially incapable of dissolving the aliphatic polyester, such as liquid paraffin, to the temperature where depolymerization takes place, and b (ml) designates the melt-phase volume of the aliphatic polyester, which is formed on heating F (g) of the aliphatic polyester in the solvent to be used actually, to the temperature where depolymerization takes place. The solvent used here is the polyalkylene glycol ether (B) alone or a combination of the polyalkylene glycol ether (B) and the solubilizing agent (C). The remaining rate of the melt phase of the aliphatic polyester is preferably 0.3 or less, more preferably 0.1 or less, and most preferably substantially zero.

In the step (III), heating of the substantially homogeneous liquid phase consisting of the aliphatic polyester (A) and the polyalkylene glycol ether (B) is continued to depolymerize the aliphatic polyester (A) and the cyclic ester formed, such as glycolide, is distilled off together with the polyalkylene glycol ether (B).

The depolymerization is a type of reaction basically shown in Equation [III] below,

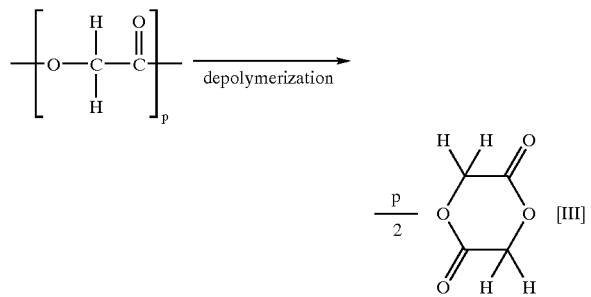

where depolymerization of polyglycolic acid (polyglycolide) is exemplified.

The heating temperature for depolymerization is equal to or higher than the temperature where depolymerization of the aliphatic polyester takes place, usually 200° C. or higher. The temperature attained by heating is usually in the range of 200–320° C., preferably 210–310° C., more preferably 220–300° C., and most preferably 230–290° C.

Heating induces depolymerization of the aliphatic polyester to form the cyclic ester and distils off the cyclic ester, such as glycolide (boiling point under atmospheric pressure: 240–241° C.) together with the solvent. When the solvent is not distilled off together with the cyclic ester, the cyclic ester is liable to deposit on the inner wall of the distilling-off line and attach itself thereto.

The temperature where the mixed solution containing the aliphatic polyester (A), the polyalkylene glycol ether (B) and optionally the solubilizing agent (C) is heated to form a substantially homogeneous liquid phase may not be always identical to the temperature where the cyclic ester, such as glycolide, formed by depolymerization is distilled off together with the polyalkylene glycol ether (B). Heating in each step may be conducted under normal or reduced pressure. Preferably, the steps (I) and (II), where the mixed solution containing the aliphatic polyester (A), the polyalkylene glycol ether (B) and optionally the solubilizing agent (C) is heated to form a substantially homogeneous liquid phase, are conducted under normal pressure, and then the step (III), where the cyclic ester is heated and distilled off together with the polyalkylene glycol ether (B), is conducted under reduced pressure. Since the depolymerization is a reversible reaction, distilling off the cyclic ester, such as glycolide, from the liquid phase makes depolymerization of the aliphatic polyester proceed efficiently.

Heating during the depolymerization may be conducted under normal or reduced pressure, but preferably under reduced pressure of 0.1–90 kPa. As the pressure is lower, the temperature for depolymerization is lower, leading to a higher rate of the solvent recovery. The pressure is preferably 1–50 kPa, more preferably 3–30 kPa, and most preferably 5–20 kPa.

The polyalkylene glycol ether (B) is typically used in a proportion of 30–500 parts by weight, and preferably 50–200 parts by weight per 100 parts by weight of the aliphatic polyester. The polyalkylene glycol ether (B) may be further added continuously or intermittently during the depolymerization reaction, so far as the mixture in the reaction system forms a substantially homogeneous liquid phase. Also, the solubilizing agent may be added into the mixture to form a more homogeneous liquid phase, and further added continuously or intermittently during the depolymerization reaction.

In the step (IV), the cyclic ester, such as glycolide, contained in the distillate may be readily separated and recovered by cooling the distillate and optionally adding a non-solvent for the cyclic ester.

The cyclic ester thus recovered may be optionally purified, for example, by recrystallization. Alternatively, the cyclic ester may be purified according to a process for purifying crude cyclic ester, as described later. On the other hand, the mother liquor left after removal of the cyclic ester contains the polyalkylene glycol ether (B) which is thermally so stable as to be little degraded and used again without subjecting it to such a step as purification. The polyalkylene glycol ether (B) may be adsorbed onto activated carbon etc. or distilled for purification before reuse.

The polyalkylene glycol ether (B) used in the present invention is stable both chemically and thermally in the depolymerization, as described above, and may be thus used again with a minimal addition of fresh polyalkylene glycol ether (B).

Since the polyalkylene glycol ether (B) used as polar organic solvent is thermally stable, in the above step (IV) according to the present invention, the distillate may be separated into liquid phases to separate and recover the cyclic ester phase, while the polyalkylene glycol ether (B) phase may be recycled into the reaction system for depolymerization.

More specifically, the distillate may be cooled through a condenser to phase separate the cyclic ester, such as glycolide, and the solvent with the liquid state kept throughout. When the distillate is phase separated, the cyclic ester phase typically forms a lower layer and the solvent phase an upper layer. The cyclic ester phase forming the lower layer may separated and recovered as liquid. Phase separation of the cyclic ester and the solvent as liquids is usually conducted by controlling the cooling temperature in the range of 85–180° C., preferably 85–150° C., and more preferably 85–120° C. If the cooling temperature is too high, undesirable reactions, such as ring opening and polymerization, are liable to occur in the cyclic ester phase during the separation procedure. If the cooling temperature is too low, their phase separation as liquids is difficult.

When the depolymerization is continued while controlling the temperature of the distillate through the condenser, the cyclic ester distilled together with the solvent passes through the upper solvent phase in drops and is condensed into the lower phase of the cyclic ester.

The polyalkylene glycol ether (B) suitable to conduct such phase separation preferably has alkyl groups within the ether groups at both ends, where the alkyl groups contain 3–21 carbons together. Such a solvent is readily phase separated from the cyclic ester, such as glycolide, at the cooling temperature described above.

The cyclic ester phase thus separated is cooled further, recovered and optionally treated for purification. In this process, it is not necessary to separate a large excess of the solvent from the cyclic ester recovered, which simplifies a procedure for separating the solvent and the cyclic ester.

Also, in this process, the polyalkylene glycol ether (B) phase may be separated from the distillate by phase separation and then returned to the reaction system for depolymerization. According to this process, it is neither necessary to recover a large amount of the solvent nor to keep a supply of the solvent more than the reactor size by volume. Thus, this process can minimize a loss of the solvent.

A combination of the polyalkylene glycol ether (B) and an alcoholic solubilizing agent may be preferably used as solvent for depolymerization of the aliphatic polyester (A), if it is a high-molecular-weight polymer with a weight-average molecular weight of 10,000–1,000,000. Also, the depolymerization is preferably conducted under reduced pressure.

Specifically, the preparation process of a cyclic ester from a high-molecular-weight aliphatic polyester (A) by depolymeriation comprises the following steps:

(i) a step of heating a mixture containing the high-molecular-weight aliphatic polyester (A), a polyalkylene glycol ether (B), which is represented by the above formula (1) and has a boiling point of 230–450° C. and a molecular weight of 150–450, and a solubilizing agent (C) of a monohydric alcohol or a polyhydric alcohol with more than one hydroxyl groups, each with a boiling point of 180° C. or higher, under normal or reduced pressure to a temperature at which depolymerization of the high-molecular-weight aliphatic polyester (A) takes place, (ii) a step of forming a substantially homogeneous solution phase consisting of the melt phase of the high-molecular-weight aliphatic polyester (A) and the liquid phase composed of the polyalkylene glycol ether (B) and the solubilizing agent (C), (iii) a step of continuing to heat the solution phase under reduced pressure to form the cyclic ester by depolymerization and distil off the cyclic ester together with the polyalkylene glycol ether (B), and (iv) a step of recovering the cyclic ester from the distillate.

According to the preparation process of the cyclic ester of the present invention, formation of tar from the aliphatic polyester hardly takes place during heating and depolymerization, resulting in saving of a work for cleaning the inner wall of the reactor. In addition, even if tar deposits in the reactor due to one accident or another, the polyalkylene glycol ether (B) and the solubilizing agent (C) may be placed in the reactor and heated to remove the tar easily.

In the case where the mother liquor left after removal of the cyclic ester contains more than one solvent and/or the solubilizing agent, the mother liquor may be recycled as solvent and/or solubilizing agent without purification, via adsorption onto activated carbon for purification, or via single or fractional distillation. The solubilizing agent dissolves tar effectively. Therefore, when the solubilizing agent is used for the depolymerization, the cleaning work for the inner wall of the reactor may be saved or reduced.

6. Purification Process of a Crude Cyclic Ester

The "solution-phase depolymerization process" of the present invention can also be applied to purification of a crude cyclic ester, such as crude glycolide.

To detail it, the present invention provides a process for purification of a crude cyclic ester, comprising the steps of heating a mixture containing the crude cyclic ester (A') and a polyalkylene glycol ether (B), which is represented by the above formula (1) and has a boiling point of 230–450° C. and a molecular weight of 150–450, under normal or reduced pressure in order to form a substantially homogeneous solution phase without phase separation of the components; continuing to heat the solution phase to distil off the cyclic ester (A) together with the polyalkylene glycol ether (B); and recovering the cyclic ester (A) from the distillate.

In the process, the cyclic ester is distilled off together with the solvent without undergoing ring-opening polymerization. The distillate is cooled and a nonsolvent for the cyclic ester is optionally added thereto, thereby separating and purifying the cyclic ester. Also, the distillate may be cooled through a condenser to induce phase separation with the liquid state kept throughout, and then the cyclic ester layer and the polyalkylene glycol ether (B) layer may be separated to recover the respective compounds.

The solvent in the mother liquor is so stable chemically and thermally as to be used again with a minimal addition of fresh polyalkylene glycol ether (B). The process for purification of a crude cyclic ester according to the present invention will be suitable for scale-up and enable a large amount of the cyclic ester to be purified industrially, as opposed to the conventional purification processes, such as a sublimation process.

7. Effects

The process for preparation of a cyclic ester according to the present invention is, so to say, "solution-phase depolymerization process". According to this process, the cyclic ester can be produced efficiently for the following reasons.

1. Since the aliphatic polyester is forced to be depolymerized in a solution phase, preferably in a homogeneous solution phase, the surface area thereof is increased much more, thereby dramatically increasing the rate of formation of the cyclic ester generated and vaporized from the surface of the aliphatic polyester.

2. Since molecules of the aliphatic polyester are difficult to contact with each other due to the dilution effect of the solvent, polycondensation of the aliphatic polyester during heating is suppressed and formation of tar is also prevented extremely. Therefore, the yield of the cyclic ester is increased and the work for cleaning the inner wall of the reactor can be saved almost completely.
3. Since the cyclic ester is formed at a temperature where the polyalkylene glycol ether (B) is distilled off and distilled off together with this solvent, accumulation thereof in the distilling-off line hardly occurs. It means prevention of the line blocking and extreme saving of the work for recovering the accumulated product in the line.
4. Since the present process can adopt a system similar to a common distillation system, it will be suitable for scale-up and mass production on an industrial scale.
5. In addition, since the polyalkylene glycol ether (B) is hardly deteriorated by heat in the depolymerization, the solvent once used for the depolymerization may be used again for the depolymerization with a minimal addition of the solvent. Consequently, mass production of the cyclic ester, such as glycolide, will greatly reduce the solvent cost and also the entire production cost.

EXAMPLES

The present invention will be described below in more detail with reference to reference examples, examples and comparative examples. In the examples below, solubilities of glycolide (a cyclic ester) in the solvents were measured by the following method.

(1) Solubility:

Into a 25-ml test tube with a common plug was put 10 ml of a solvent, and then glycolide was added in an amount controlled just above saturation. The mixture was treated supersonically for 30 minutes. After the treatment, it was left at 25° C. overnight. The supernatant was then analyzed quantitatively for glycolide content by gas chromatography. Then, the total weight B (g) of glycolide in the solution was determined. Finally, the solubility of glycolide was calculated according to the following equation.

Solubility(%)=(B/10)×100

Reference Example 1
Synthesis of a Glycolic Acid Oligomer

A 5-liter autoclave was charged with 2,500 g of glycolic acid (product of Wako Pure Chemical Industries, Ltd.). While stirring under normal pressure, the temperature of the contents was raised from 170° C. to 200° C. over 2 hours to heat them, whereby glycolic acid was subjected to condensation reaction while distilling out water formed. The pressures inside the autoclave was then reduced to 5.0 kPa, and the reaction product was heated at 200° C. for 2 hours, thereby distilling off low-boiling matter such as an unreacted raw material to prepare a glycolic acid oligomer.

The melting point (Tm) of the glycolic acid oligomer thus obtained was 206° C., and its ΔHmc was 105 J/g. Incidentally, Tm is a value detected when the oligomer is heated at a rate of 10° C./min in an inert gas atmosphere by means of a DSC, and the ΔHmc is a melt enthalpy detected at the time.

Reference Example 2
Synthesis of Tetraethylene Glycol Dibutyl Ether (TEG-DB)

Into a flask were put 500 ml of toluene, 118.2 g of butoxyethanol and 101.2 g of triethylamine, and 115 g of methanesulfonyl chloride was added dropwise to the mixture cooled by ice. Triethylamine hydrochloride was precipitated and removed, and then 206.3 g of triethylene glycol butyl ether was added. The mixture was transferred into a dropping funnel, and then added into a mixed solution of 40 g of 60% NaH and 200 ml of toluene at 60–70° C. Tetraethylene glycol dibutyl ether was obtained by distillation (boiling point (b.p.): 140–143° C. at 80 Pa) from the reaction solution. This compound (abbreviated as "TEG-DB" hereafter) has a corresponding boiling point of about 340° C. under normal pressure. Further, the solubility of glycolide in this compound at 25° C. was 4.6%.

Reference Example 3
Synthesis of Diethylene Glycol Butyl 2-Chlorophenyl Ether (DEG-BClPh)

Into a flask were put 330.9 g of ethylene glycol n-butyl ether, 202.3 g of triethylamine and 500 ml of toluene, and the mixture was cooled by ice with stirring, where 229.1 g of methanesulfonyl chloride was added dropwise in 4 h keeping the temperature at 7–10° C. The reaction mixture was warmed back to room temperature and kept at the temperature to continue the reaction for 2 h. Water was added to the reaction mixture to separate the toluene phase. Then, toluene was evaporated from the phase to obtain 474.7 g of the mesylate.

Subsequently, a mixture of 78.2 g of NaOH and 117 g of water was added in halves twice to a mixture of 470 g of the above mesylate, 260 g of 2-chlorophenol and 20 ml of N-methylpyrrolidone, which was heated to 100° C. Further, a mixture of 18.7 g of NaOH and 59 g of water was added to continue the reaction for 1 h. After the mixture was washed with water, 519.7 g of the object compound, diethylene glycol butyl 2-chlorophenyl ether was obtained by distillation (b.p.: 139–144° C. at 70 Pa) of the toluene phase. This compound (abbreviated as "DEG-BClPh" hereafter) has a corresponding boiling point of about 345° C. under normal pressure. The solubility of glycolide in this compound at 25° C. was 1.8%.

Reference Example 4

Synthesis of Diethylene Glycol Dibutyl Ether (DEG-DB)

Into 120 g of 60% NaH and 500 ml of toluene were added dropweise 329 g of butyl bromide and 486 g of diethylene glycol butyl ether at 50° C. Diethylene glycol dibutyl ether (abbreviated as "DEG-DB" hereafter) was obtained by distillation (b.p.: 256° C. under normal pressure) from the reaction mixture. The solubility of glycolide in this compound at 25° C. was 1.8%.

Reference Example 5

Synthesis of Triethylene Glycol n-butyl n-octyl Ether (TEG-BO)

The procedure followed that of Reference Example 4, except for use of n-octyl bromide and triethylene glycol n-butyl ether instead of butyl bromide and diethylene glycol butyl ether, respectively. Triethylene glycol n-butyl n-octyl ether (abbreviated as "TEG-BO" hereafter) was obtained by distillation (b.p.: 140–145° C. at 70 Pa). TEG-BO has a corresponding boiling point of about 350° C. under normal pressure. The solubility of glycolide in this compound at 25° C. was 2.0%.

Reference Example 6

Synthesis of Triethylene Glycol Butyl Decyl Ether (TEG-BD)

The procedure followed that of Reference Example 5, except for use of decyl bromide instead of octyl bromide.

Triethylene glycol butyl decyl ether (abbreviated as "TEG-BD" hereafter) was obtained by distillation (b.p.: 170–180° C. at 70 Pa). TEG-BD has a corresponding boiling point of about 400° C. under normal pressure. The solubility of glycolide in this compound at 25° C. was 1.3%.

The results are shown together in Table 1.

TABLE 1

| Reference Example | $X^1$ | Y | $R^1$ | P | Boiling point (° C.) | Molecular weight | Solubility of glycolide (%) | Code of polyalkylene glycol ether |
|---|---|---|---|---|---|---|---|---|
| 2 | Bu | Bu | Ety | 4 | 340 | 306 | 4.6 | TEC-DB |
| 3 | Bu | 2-ClPh | Ety | 2 | 345 | 273 | 1.8 | DEG-BClPh |
| 4 | Bu | Bu | Ety | 2 | 256 | 218 | 1.8 | DEG-DB |
| 5 | Bu | Oct | Ety | 3 | 350 | 318 | 2.0 | TEG-BO |
| 6 | Bu | Dec | Ety | 3 | 400 | 347 | 1.3 | TEG-BD |

Note:
Bu is an abbreviation for a butyl group,
2-ClPh for a 2-chlorophenyl group,
Oct for an octyl group,
Dec for a decyl group, and
Ety for —$CH_2CH_2$—.

Example 1

A 300-ml flask, to which a receiver cooled with chilled water was connected, was charged with 40 g of the glycolic acid oligomer prepared in Reference Example 1. Then, 200 g of tetraethylene glycol dibutyl ether (TEG-DB) prepared in Reference Example 2 was added as solvent, polyalkylene glycol ether (B). The mixture of the glycolic acid oligomer and the solvent was heated to 280° C. in a nitrogen gas atmosphere. It was visually confirmed that the glycolic acid oligomer dissolved homogeneously in the solvent substantially without undergoing phase separation. While the mixture was heated longer and subjected to a reduced pressure of 10 kPa, depolymerization was initiated to distill out glycolide formed together with the solvent. The depolymerization was completed in about 4 hours.

After the co-distillation was finished, the glycolide that had deposited from the distillate was separated and recrystallized from ethyl acetate. The glycolide obtained after it was dried weighed 26 g (yield: 65%) and it was found highly pure since its purity (by area) was 99.98% by gas chromatographic (GC) analysis. The TEG-DB remaining together in the mother liquor and in the reaction solution was determined at 198 g (the remaining rate: 99%) by GC analysis, indicating minimal loss of the solvent.

Example 2

A 300-ml flask, to which a receiver cooled with chilled water was connected, was charged with 20 g of the glycolic acid oligomer prepared in Reference Example 1. Then, 180 g of diethylene glycol butyl 2-chlorophenyl ether (DEG-BClPh) prepared in Reference Example 3 was added as solvent, polyalkylene glycol ether (B). The mixture of the glycolic acid oligomer and the solvent was heated to 280° C. in a nitrogen gas atmosphere. It was visually confirmed that the glycolic acid oligomer dissolved nearly homogeneously in the solvent substantially without undergoing phase separation. While the mixture was heated longer and subjected to a reduced pressure of 8 kPa, depolymerization was initiated to distill out glycolide formed together with the solvent. The depolymerization was completed in about 4 hours.

After the co-distillation was finished, the glycolide that had deposited from the distillate was separated and recrystallized from ethyl acetate. The glycolide obtained after it was dried weighed 12 g (yield: 60%) and it was found highly pure since its purity (by area) was 99.98% by GC analysis. The DEG-BClPh remaining together in the mother liquor and in the reaction solution was determined at 173 g (the remaining rate: 96%) by GC analysis, indicating minimal loss of the solvent.

Example 3

A 300-ml flask, to which a receiver cooled with chilled water was connected, was charged with 20 g of the glycolic acid oligomer prepared in Reference Example 1. Then, 200 g of diethylene glycol dibutyl ether (DEG-DB) prepared in Reference Example 4 was added as solvent, polyalkylene glycol ether (B). The mixture of the glycolic acid oligomer and the solvent was heated to 260° C. in a nitrogen gas atmosphere. It was visually confirmed that the glycolic acid oligomer dissolved nearly homogeneously in the solvent substantially without undergoing phase separation. While the mixture was heated longer and subjected to a reduced pressure of 20 kPa, depolymerization was initiated to distill out glycolide formed together with the solvent. The depolymerization was completed in about 4 hours.

After the co-distillation was finished, the glycolide that had deposited from the distillate was separated and recrystallized from ethyl acetate. The glycolide obtained after it was dried weighed 11 g (yield: 55%) and it was found highly pure since its purity (by area) was 99.96% by GC analysis. The DEG-DB remaining together in the mother liquor and in the reaction solution was determined at 198 g (the remaining rate: 99%) by GC analysis, indicating minimal loss of the solvent.

Example 4

A 300-ml flask, to which a receiver cooled with chilled water was connected, was charged with 40 g of the glycolic acid oligomer prepared in Reference Example 1. Then, 200 g of diethylene glycol dibutyl ether (DEG-DB) prepared in Reference Example 4 was added as solvent, polyalkylene glycol ether (B) and 50 g of polyethylene glycol dimethyl ether #2000 (average molecular weight (M.W.): 2000, from Merck) was also added as solubilizing agent (C). The mixture of the glycolic acid oligomer and the solvent was heated to 260° C. in a nitrogen gas atmosphere. It was visually confirmed that the glycolic acid oligomer dissolved homogeneously in the solvent without undergoing phase separation. While the mixture was heated longer and subjected to a reduced pressure of 20 kPa, depolymerization was initiated to distill out glycolide formed together with the solvent. The depolymerization was completed in about 5 hours.

After the co-distillation was finished, the glycolide that had deposited from the distillate was separated and recrystallized from ethyl acetate. The glycolide obtained after it was dried weighed 32 g (yield: 80%) and it was found highly pure since its purity (by area) was 99.98% by GC analysis. The DEG-DB remaining together in the mother liquor and in the reaction solution was determined at 199 g (the remaining rate: 99.5%) by GC analysis, indicating minimal loss of the solvent.

Example 5

Depolymerization was conducted according to Example 4, except for use of 10 g of tetraethylene glycol (M.W.: 194 and b.p.: 327° C.) as alternative solubilizing agent (C). After the co-distillation was finished, the glycolide that had deposited from the distillate was separated and recrystallized from ethyl acetate. The glycolide obtained after it was dried weighed 30 g (yield: 75%) and it was found highly pure since its purity (by area) was 99.96% by GC analysis. The DEG-DB remaining together in the mother liquor and in the reaction solution was determined at 199 g (the remaining rate: 99.5%) by GC analysis, indicating minimal loss of the solvent.

Example 6

Depolymerization was conducted according to Example 4, except for use of 60 g of polyethylene glycol #600 (average M.W.: 600) as alternative solubilizing agent (C). After the co-distillation was finished, the glycolide that had deposited from the distillate was separated and recrystallized from ethyl acetate. The glycolide obtained after it was dried weighed 32 g (yield: 80%) and it was found highly pure since its purity (by area) was 99.98% by GC analysis. The DEG-DB remaining together in the mother liquor and in the reaction solution was determined at 199 g (the remaining rate: 99.5%) by GC analysis, indicating minimal loss of the solvent.

Example 7

Depolymerization was conducted according to Example 4, except for use of 40 g of polypropylene glycol #400 (average M.W.: 400) as alternative solubilizing agent (C). After the co-distillation was finished, the glycolide that had deposited from the distillate was separated and recrystallized from ethyl acetate. The glycolide obtained after it was dried weighed 33 g (yield: 82.5%) and it was found highly pure since its purity (by area) was 99.97% by GC analysis. The DEG-DB remaining together in the mother liquor and in the reaction solution was determined at 199 g (the remaining rate: 99.5%) by GC analysis, indicating minimal loss of the solvent.

Example 8

A 300-ml flask, to which a receiver cooled with chilled water was connected, was charged with 40 g of the glycolic acid oligomer prepared in Reference Example 1. Then, 100 g of triethylene glycol butyl octyl ether (TEG-BO) prepared in Reference Example 5 was added as solvent, polyalkylene glycol ether (B) and 50 g of polyethylene glycol monomethyl ether #350 (average M.W.: 350, from Aldrich) was also added as solubilizing agent (C). The mixture of the glycolic acid oligomer and the solvent was heated to 260° C. in a nitrogen gas atmosphere. It was visually confirmed that the glycolic acid oligomer dissolved homogeneously in the solvent substantially without undergoing phase separation. While the mixture was heated longer and subjected to a reduced pressure of 10 kPa, depolymerization was initiated to distill out glycolide formed together with the solvent. During the reaction, 100 g of TEG-BO was added further. The depolymerization was completed in about 7 hours.

After the co-distillation was finished, the glycolide that had deposited from the distillate was separated and recrystallized from ethyl acetate. The glycolide obtained after it was dried weighed 32 g (yield: 80%) and it was found highly pure since its purity (by area) was 99.99% by GC analysis. The TEG-BO remaining together in the mother liquor and in the reaction solution was determined at 198 g (the remaining rate: 99%) by GC analysis, indicating minimal loss of the solvent.

Example 9

A 300-ml flask, to which a receiver cooled with chilled water was connected, was charged with 40 g of the glycolic acid oligomer prepared in Reference Example 1. Then, 80 g of triethylene glycol butyl decyl ether (TEG-BD) prepared in Reference Example 6 was added as solvent, polyalkylene glycol ether (B) and 50 g of polyethylene glycol monolauryl ether (trade name: Newcol 1105, from Nippon Nyukazai Co., Ltd.) was also added as solubilizing agent (C). The mixture of the glycolic acid oligomer and the solvent was heated to 280° C. in a nitrogen gas atmosphere. It was visually confirmed that the oligomer dissolved homogeneously in the solvent substantially without undergoing phase separation. While the mixture was heated longer and subjected to a reduced pressure of 8 kPa, depolymerization was initiated to distill out glycolide formed together with the solvent. During the reaction, 100 g of TEG-BD was added further portionwise. The depolymerization was completed in about 7 hours.

After the co-distillation was finished, the glycolide that had deposited from the distillate was separated and recrystallized from ethyl acetate. The glycolide obtained after it was dried weighed 33 g (yield: 82.5%) and it was found highly pure since its purity (by area) was 99.99% by GC analysis. The TEG-BD remaining together in the mother liquor and in the reaction solution was determined at 175 g (the remaining rate: 94%) by GC analysis, indicating minimal loss of the solvent. In addition, the inner wall of the reactor was almost free of any foul matter and cleaner than that in any one of Examples 1–8, resulting in no necessity of cleaning it.

Comparative Example 1

A 300-ml flask, to which a receiver cooled with chilled water was connected, was charged with 40 g of the glycolic acid oligomer prepared in Reference Example 1. Then, 170 g of di(2-methoxyethyl) phthalate (DMEP) was added as polar organic solvent. The mixture of the glycolic acid oligomer and the solvent was heated to 280° C. in a nitrogen gas atmosphere. It was visually confirmed that the glycolic acid oligomer dissolved homogeneously in the solvent substantially without undergoing phase separation. While the mixture was heated longer and subjected to a reduced pressure of 13 kPa, depolymerization was initiated to distill out glycolide formed together with the solvent. The depolymerization was completed in about 4 hours.

After the co-distillation was finished, the glycolide that had deposited from the distillate was separated and recrystallized from ethyl acetate. The glycolide obtained after it was dried weighed 25 g (yield: 62.5%) and its purity (by area) was 99.85% by GC analysis. The DMEP remaining together in the mother liquor and in the reaction solution was determined at 125 g (the remaining rate: 73%) by GC analysis. Also, phthalic anhydride and 2-methoxyethanol were found in the mother liquor.

Results from Examples 1–9 and Comparative Example 1 are shown together in Table 2.

TABLE 2

| No. of Example | Solvent Type[1] | Solvent Boiling point[2] (° C.) | Solvent Amount[3] | Solubilizing agent Type[1] | Solubilizing agent Molecular Weight | Solubilizing agent Amount[3] | Conditions for dissolution Temperature (° C.) | Conditions for dissolution Pressure | Conditions for depolymerization Temperature (° C.) | Conditions for depolymerization Pressure (kPa) | Yield of glycolide (%) | Remaining rate of solvent (%) | Remaining rate of melt phase |
|---|---|---|---|---|---|---|---|---|---|---|---|---|---|
| Example 1 | TEG-DB | 340 | 500 | — | — | — | 280 | Normal | 280 | 10 | 65.0 | 99.0 | 0.2 |
| Example 2 | DEG-BClPh | 345 | 900 | — | — | — | 280 | Normal | 280 | 8 | 60.0 | 96.0 | 0.3 |
| Example 3 | DEG-DB | 256 | 1000 | — | — | — | 260 | Normal | 260 | 20 | 55.0 | 99.0 | 0.1 |
| Example 4 | DEG-DB | 256 | 500 | PEGDME | 2000 | 125 | 260 | Normal | 260 | 20 | 80.0 | 99.5 | 0 |
| Example 5 | DEG-DB | 256 | 500 | TEG | 194 | 25 | 260 | Normal | 260 | 20 | 75.0 | 99.5 | 0 |
| Example 6 | DEG-DB | 256 | 500 | PEG | 600 | 150 | 260 | Normal | 260 | 20 | 80.0 | 99.5 | 0 |
| Example 7 | DEG-DB | 256 | 500 | PPG | 400 | 100 | 260 | Normal | 260 | 20 | 82.5 | 99.5 | 0 |
| Example 8 | TEG-BO | 350 | 500 | PEGMME | 350 | 125 | 260 | Normal | 260 | 10 | 80.0 | 99.0 | 0 |
| Example 9 | TEG-BD | 400 | 450 | PEGMLE | 318 | 125 | 280 | Normal | 280 | 8 | 82.5 | 94.0 | 0 |
| Comp. Exam. 1 | DMEP | 320 | 425 | — | — | — | 280 | Normal | 280 | 13 | 62.5 | 73.0 | 0 |

Note:
[1] the type of solvent is expressed by abbreviation as TEG-DB for tetraethylene glycol dibutyl ether, DEG-BClPh for diethylene glycol butyl 2-chlorophenyl ether, DEG-DB for diethylene glycol dibutyl ether, TEG-BO for triethylene glycol butyl octyl ether, TEG-BD for triethylene glycol butyl decyl ether, or DMEP for di(2-methoxyethyl) phthalate; and the type of solubilizing agent is expressed similarly as PEGDME for polyethylene glycol dimethyl ether, TEG for tetraethylene glycol, PEG for polyethylene glycol, PPG for polypropylene glycol, PEGMME for polyethylene glycol monomethyl ether, and PEGMLE for polyethylene glycol monolauryl ether;
[2] the boiling point of solvent is a value to be indicated under normal pressure; and
[3] the amount of solvent or solubilizing agent is expressed as parts by weight per 100 parts by weight of glycolic acid oligomer.

Example 10

According to Example A described in U.S. Pat. No. 2,668,162, 100 g of glycolic acid oligomer, prepared by condensation of glycolic acid, was ground to powders and mixed with 1 g of antimony trioxide. The mixture was introduced into a reactor in 5 portions at a rate of 20 g/h, while heating the reactor to 270–280° C. and keeping its interior at a reduced pressure of 10–15 mmHg. Yellow distillate thus formed was cooled to obtain 87 g of crude glycolide. A 300-ml flask, to which a receiver cooled with chilled water was connected, was charged with 40 g of the crude glycolide (97% pure by the peak area of GC). Then, 200 g of tetraethylene glycol dibutyl ether (TEG-DB) prepared in Reference Example 2 was added as solvent, polyalkylene glycol ether (B). The mixture of the crude glycolide and the solvent was heated to 250° C. in a nitrogen gas atmosphere. It was visually confirmed that the crude glycolide dissolved homogeneously in the solvent without undergoing phase separation. While the mixture was heated longer and subjected to a reduced pressure of 7 kPa, glycolide began to be distilled out together with the solvent. The co-distillation was completed in about 4 h.

After the co-distillation was finished, the glycolide that had deposited from the distillate was separated and recrystallized from ethyl acetate. The glycolide obtained after it was dried weighed 36 g (yield: 90%) and it was found highly pure since its purity (by area) was 99.99% by GC analysis. The TEG-DB remaining together in the mother liquor and in the reaction solution was determined at 198 g (the remaining rate: 99%) by GC analysis, indicating minimal loss of the solvent.

Comparative Example 2

A 300-ml flask, to which a receiver cooled with chilled water was connected, was charged with 40 g of the crude glycolide (97% pure by the peak area of GC) prepared according to Example 10. Then, 170 g of di(2-methoxyethyl) phthalate (DMEP) was added as polar organic solvent. The mixture of the crude glycolide and the solvent was heated to 250° C. in a nitrogen gas atmosphere. It was visually confirmed that the crude glycolide dissolved homogeneously in the solvent substantially without undergoing phase separation. While the mixture was heated longer and subjected to a reduced pressure of 7 kPa, glycolide began to be distilled out together with the solvent. The co-distillation was completed in about 4 h. After the co-distillation was finished, the glycolide that had deposited from the distillate was separated and recrystallized from ethyl acetate. The glycolide obtained after it was dried weighed 32 g (yield: 80%) and its purity (by area) was 99.92% by GC analysis. The DMEP remaining together in the mother liquor and in the reaction solution was determined at 142 g (the remaining rate: 84%) by GC analysis. Also, phthalic anhydride and 2-methoxyethanol were found in the mother liquor.

Results from Example 10 and Comparative Example 1 are shown together in Table 3.

TABLE 3

| No. of Example | Solvent Type[1] | Solvent Boiling point[2] (° C.) | Solvent Amount[3] | Conditions for dissolution Temperature (° C.) | Conditions for dissolution Pressure | Conditions for depolymerization Temperature (° C.) | Conditions for depolymerization Pressure (kPa) | Yield of glycolide (%) | Remaining rate of solvent (%) |
|---|---|---|---|---|---|---|---|---|---|
| Exam. 10 | TEG-DB | 340 | 500 | 250 | Normal | 250 | 7 | 90 | 99 |
| Comp. Exam. 2 | DMEP | 320 | 425 | 250 | Normal | 250 | 7 | 80 | 84 |

Note:
[1] the type of solvent is expressed by abbreviation as TEG-DB for tetraethylene glycol dibutyl ether, or DMEP for di(2-methoxyethyl) phthalate;
[2] the boiling point of solvent is a value to be indicated under normal pressure; and
[3] the amount of solvent or solubilizing agent is expressed as parts by weight per 100 parts by weight of glycolic acid oligomer.

Example 11

Phase Separation of Distillate

A 300-ml flask, to which a Dien-Stark-type receiver heated with hot water at 90° C. and equipped with a condenser was connected, was charged with 80 g of the glycolic acid oligomer prepared in Reference Example 1. Then, 200 g of diethylene glycol butyl 2-chlorophenyl ether (DEG-BClPh) prepared in Reference Example 3 was added as solvent, polyalkylene glycol ether (B), and 60 g of polyethylene glycol #600 (average M.W.: 600) was also added as solubilizing agent (C). The mixture of the glycolic acid oligomer and the solvent was heated to 260° C. in a nitrogen gas atmosphere. It was visually confirmed that the glycolic acid oligomer dissolved homogeneously in the solvent substantially without undergoing phase separation. While the mixture was heated longer and subjected to a reduced pressure of 10 kPa, depolymerization was initiated to distill out glycolide formed together with the solvent.

The distillate was cooled through the condenser to lower the temperature to 100° C., resulting in phase separation forming two liquid phases, of which the upper layer is a solvent phase and the lower layer is aglycolide phase. While the depolymerization was still continued after formation of the two liquid phases, glycolide, just formed, distilled and cooled through the condenser, could be then observed to pass dropwise through the solvent phase and condense into the lower layer of the glycolide phase. The upper layer of the solvent phase was returned by reflux continuously into the reaction system.

Just before the receiver was filled with the glycolide melt phase, the pressure within the reaction system was temporarily raised to normal pressure, the glycolide melt was then drawn through the outlet at the bottom. Then, the system was evacuated down to the pressure reached before to start depolymerization again. About 3 hours later, the reaction was stopped when little amount of glycolide was seen to be distilled out.

The glycolide melt recovered weighed 64.5 g. GC analysis indicated that 0.3 g of DEG-BClPh was present in the glycolide melt. The glycolide melt was cooled for solidification and the solid was recrystallized from ethyl acetate. The glycolide obtained after it was dried weighed 64.2 g (yield: 80%) and it was found highly pure since its purity (by area) was 99.98% by GC analysis. The DEG-BClPh remaining together in the glycolide melt and in the reaction solution was determined at 199 g (the remaining rate: 99.5%) by GC analysis, indicating minimal loss of the solvent.

Example 12

Depolymerization of High-Molecular-Weight Polyglycolic Acid

A 300-ml flask, to which a receiver cooled with chilled water was connected, was charged with 20 g of polyglycolic acid granules with weight-averaged molecular weight of 200,000. Then, 200 g of diethylene glycol dibutyl ether (DEG-DB) prepared in Reference Example 4 was added as solvent, polyalkylene glycol ether (B) and 50 g of polyethylene glycol #600 (average M.W.: 600) was also added as solubilizing agent (C). The mixture of the polyglycolic acid and the solvent was heated to 260° C. in a nitrogen gas atmosphere. It was visually confirmed that the polyglycolic acid dissolved nearly homogeneously in the solvent substantially without undergoing phase separation. While the mixture was heated longer and subjected to a reduced pressure of 20 kPa, depolymerization was initiated to distill out glycolide formed together with the solvent. The depolymerization was completed in about 4 h.

After the co-distillation was finished, the glycolide that had deposited from the distillate was separated and recrystallized from ethyl acetate. The glycolide obtained after it was dried weighed 11 g (yield: 55%) and it was found highly pure since its purity (by area) was 99.96% by GC analysis. The DEG-DB remaining together in the mother liquor and in the reaction solution was determined at 198 g (the remaining rate: 99%) by GC analysis, indicating minimal loss of the solvent.

Example 13

Depolymerization of High-Molecular-Weight Polyglycolic Acid

A cylinder of polyglycolic acid, 30 cm long and 2 cm in diameter, was cut into pieces 1 cm long. A 300-ml flask, to which a receiver cooled with chilled water was connected, was charged with 20 g of the pieces. Then, 200 g of diethylene glycol dibutyl ether (DEG-DB) prepared in Reference Example 4 was added as solvent, polyalkylene glycol ether (B) and 50 g of polyethylene glycol #600 (average M.W.: 600) was also added as solubilizing agent (C). The mixture of the polyglycolic acid and the solvent was heated to 260° C. in a nitrogen gas atmosphere. It was visually confirmed that the polyglycolic acid dissolved nearly homogeneously in the solvent within 30 minutes substantially without undergoing phase separation. While the mixture was heated longer and subjected to a reduced pressure of 20 kPa, depolymerization was initiated to distill out glycolide formed together with the solvent. The depolymerization was completed in about 4 hours.

After the co-distillation was finished, the glycolide that had deposited from the distillate was separated and recrystallized from ethyl acetate. The glycolide obtained after it was dried weighed 10.5 g (yield: 52.5%) and it was found highly pure since its purity (by area) was 99.97% by GC analysis. The DEG-DB remaining together in the mother liquor and in the reaction solution was determined at 198 g (the remaining rate: 99%) by GC analysis, indicating minimal loss of the solvent.

Example 14

Depolymerization of Polylactic Acid

A 300-ml flask, to which a receiver cooled with chilled water was connected, was charged with 20 g of pelletized polylactic acid (LACTY #9400 with weight-averaged molecular weight of 200,000; from Shimadzu). Then, 200 g of triethylene glycol butyl octyl ether (TEG-BO) prepared in Reference Example 5 was added as solvent, polyalkylene glycol ether (B) and 50 g of polyethylene glycol #400 (average M.W.: 400) was also added as solubilizing agent (C). The mixture of the polylactic acid and the solvent was heated to 230° C. in a nitrogen gas atmosphere. It was visually confirmed that the polylactic acid dissolved nearly homogeneously in the solvent substantially without undergoing phase separation. While the mixture was heated longer and subjected to a reduced pressure of 4 kPa, depolymerization was initiated to distill out lactide formed together with the solvent. The depolymerization was completed in about 3 hours.

After the co-distillation was finished, the lactide that had deposited from the distillate was separated and recrystallized from diethyl ether. The lactide obtained after it was dried weighed 13 g (yield: 65%) and it was found highly pure since its purity (by area) was 99.97% by GC analysis. The TEG-BO remaining together in the mother liquor and in the reaction solution was determined at 198 g (the remaining rate: 99%) by GC analysis, indicating minimal loss of the solvent.

Industrial Applicability

The present invention can provide a cyclic ester industrially by efficiently and economically depolymerizing an aliphatic polyester including from low-molecular-weight material such as oligomer to high-molecular-weight material. The present invention also provides a process for efficiently and economically purifying a crude cyclic ester.

In particular, the production process of a cyclic ester according to the present invention depolymerizes an aliphatic polyester in a solution phase formed by a specific polyalkylene glycol ether used as solvent to produce a highly pure cyclic ester efficiently. In addition, the present process can suppress formation of tar minimally, improve the yield of the cyclic ester product and extremely save a work for cleaning the inner wall of the reactor.

Since the cyclic ester is formed at a temperature where the specific polyalkylene glycol ether is distilled out and distilled out together with the polyalkylene glycol ether, blocking thereby of the recovery line is prevented and therefore accumulation of any matter on the inner wall of the line hardly occurs, resulting in no practical necessity of recovering the matter.

Since the present process can employ a system similar to a common distillation system, it can be easily adapted to scale-up and mass production on an industrial scale. In addition, since the specific polyalkylene glycol ether used as solvent is hardly deteriorated by heat in the depolymerization, the solvent once used for the depolymerization may be used again for the depolymerization with a minimal addition of the fresh solvent. Consequently, mass production of the cyclic ester will be attained at a low cost.

Further, the present process can utilize product wastes after use, mold wastes and the likes made of high-molecular-weight aliphatic polyester, etc. to convert them into cyclic ester as monomer for recycling.

The present process provides a cyclic ester which can be used as starting material for an aliphatic polyester suitable as biodegradable polymeric material, medical material, etc.

What is claimed is:

1. A process for production of a cyclic ester by depolymerization of an aliphatic polyester, which comprises the steps of:

(I) heating a mixture containing the aliphatic polyester (A) and a polyalkylene glycol ether (B), which is represented by the following formula (1)

(1)

where $R^1$ is a methylene group, or a straight-chain or branched-chain alkylene group with 2–8 carbons, $X^1$ is a hydrocarbon group, Y is an alkyl or aryl group with 2–20 carbons, p is an integer not smaller than 1 and when p is 2 or greater, a plurality of $R^1$ groups may be identical or different, and has a boiling point of 230–450° C. and a molecular weight of 150–450, under normal or reduced pressure to a temperature at which depolymerization of said aliphatic polyester (A) takes place, (II) forming a substantially homogeneous solution phase consisting of the melt phase of said aliphatic polyester (A) and the liquid phase of said polyalkylene glycol ether (B), (III) continuing to heat said solution phase to form the cyclic ester by depolymerization and distil out the cyclic ester together with said polyalkylene glycol ether (B), and (IV) recovering the cyclic ester from the distillate, wherein said polyalkylene glycol ether (B) is a polyalkylene glycol ether in which the cyclic ester is soluble in the range of 0.1–10% at 25° C.

2. The process for production according to claim 1, wherein said aliphatic polyester (A) is a polyhydroxycarboxylic acid.

3. The process for production according to claim 2, wherein said polyhydroxycarboxylic acid is a poly(α-hydroxycarboxylic acid).

4. The process for production according to claim 3, wherein said poly(α-hydroxycarboxylic acid) is polyglycolic acid or polylactic acid.

5. The process for production according to claim 1, wherein said aliphatic polyester (A) is a low-molecular-weight material with a weight-averaged molecular weight less than 10,000.

6. The process for production according to claim 1, wherein said aliphatic polyester (A) is a high-molecularweight material with a weight-averaged molecular weight equal to 10,000 or higher.

7. The process for production according to claim 1, wherein said polyalkylene glycol ether (B) is a polyalkylene glycol ether where $R^1$ is a alkylene group with 2–5 carbons in said formula (1).

8. The process for production according to claim 1, wherein said polyalkylene glycol ether (B) is a polyalkylene glycol ether where both $X^1$ and Y are alkyl groups containing 3–21 carbons together in said formula (1).

9. The process for production according to claim 1, wherein said polyalkylene glycol ether (B) is a polyethylene glycol dialkyl ether.

10. The process for production according to claim 9, wherein said polyethylene glycol dialkyl ether is diethylene glycol dialkyl ether, triethylene glycol dialkyl ether or tetraethylene glycol dialkyl ether.

11. The process for production according to claim 1, wherein said polyalkylene glycol ether (B) is tetraethylene glycol dibutyl ether, diethylene glycol butyl 2-chlorophenyl ether, diethylene glycol dibutyl ether, triethylene glycol n-butyl n-octyl ether or triethylene glycol butyl decyl ether.

12. The process for production according to claim 1, wherein said polyalkylene glycol ether (B) is mixed with said aliphatic polyester (A) in a proportion of 30–500 parts by weight per 100 parts by weight of said aliphatic polyester (A) in said step (I).

13. The process for production according to claim 1, wherein said mixture is heated at a temperature in the range of 200–320° C. in said steps (I) to (III).

14. The process for production according to claim 1, wherein the heating is continued under a reduced pressure in the range of 0.1–90 kPa in said step (III).

15. The process for production according to claim 1, wherein said mixture also contains a solubilizing agent (C) to increase the solubility of said aliphatic polyester (A) in said polyalkylene glycol ether (B) in either or both of said steps (I) and (II).

16. The process for production according to claim 15, wherein said solubilizing agent (C) has a boiling point of at least 180° C. and is a non-basic compound miscible with said polyalkylene glycol ether (B).

17. The process for production according to claim 15, wherein said solubilizing agent (C) is at least one compound selected from a group consisting of monohydric alcohols or polyhydric alcohols with at least two hydroxyl groups (including partial esters or ethers thereof), phenols, aliphatic monocarboxylic acids or aliphatic polycarboxylic acids with at least two carboxyl groups, aliphatic amides, which are derived from an aliphatic carboxylic acid and an amine, aliphatic imides, and polyalkylene glycol ethers with molecular weight more than 450.

18. The process for production of glycolide according to claim 15, wherein said solubilizing agent (C) is a polyalkylene glycol represented by the following formula (2)

(2)

where $R^1$ is a methylene group, or a straight-chain or branched-chain alkylene group with 2–8 carbons, q is an integer not smaller than 1 and when q is 2 or greater, a plurality of $R^2$ groups may be identical or different.

19. The process for production according to claim 18, wherein said polyalkylene glycol is at least one compound selected from a group consisting of polyethylene glycol, polypropylene glycol and polybutylene glycol.

20. The process for production according to claim 15, wherein said solubilizing agent (C) is a polyalkylene glycol monoether represented by the following formula (3)

(3)

where $R^3$ is a methylene group, or a straight-chain or branched-chain alkylene group with 2–8 carbons, $X^2$ is a hydrocarbon group, r is an integer not smaller than 1 and when r is 2 or greater, a plurality of $R^3$ groups may be identical or different.

21. The process for production according to claim 20, wherein said polyalkylene glycol monoether is at least one compound selected from a group consisting of polyethylene glycol monoether, polypropylene glycol monoether and polybutylene glycol monoether.

22. The process for production according to claim 20, wherein said polyethylene glycol monoether has an alkyl group with 1–18 carbons within the terminal ether group.

23. The process for production according to claim 15, wherein said solubilizing agent (C) is added in a proportion of 0.1–500 parts by weight per 100 parts by weight of said aliphatic polyester (A).

24. The process for production according to claim 1, wherein, in the step (IV), said distillate is cooled through a condenser to phase separate said cyclic ester and said polyalkylene glycol ether (B) with the liquid state kept throughout, and separate and recover the cyclic ester phase.

25. The process for production according to claim 24, wherein said distillate is cooled to a temperature in the range of 85–180° C. to phase separate said cyclic ester and said polyalkylene glycol ether (B) as liquids.

26. The process for production according to claim 24, wherein the depolymerization is continued with simultaneous phase separation, and said cyclic ester contained in the distillate is condensed into the lower layer of the cyclic ester phase.

27. The process for production according to claim 24, wherein the polyalkylene glycol ether (B) phase is separated and returned to the reaction system of said depolymerization.

28. A process for production of a cyclic ester by depolymerization of a high-molecular-weight aliphatic polyester with a weight-averaged molecular weight of 10,000 or more, which comprises:

(i) a step of heating a mixture containing a high-molecular-weight aliphatic polyester (A), a polyalkylene glycol ether (B), which is represented by the following formula (1)

(1)

where $R^1$ is a methylene group, or a straight-chain or branched-chain alkylene group with 2–8 carbons, $X^1$ is a hydrocarbon group, Y is an alkyl or aryl group with 2–20 carbons, p is an integer not smaller than 1 and when p is 2 or greater, a plurality of $R^1$ groups may be identical or different, and has a boiling point of 230–450° C. and a molecular weight of 150–450, and a solubilizing agent (C) of a monohydric alcohol or a polyhydric alcohol with at least two hydroxyl groups, each with a boiling point of 180° C. or higher, under normal or reduced pressure to a temperature at which depolymerization of the high-molecular-weight aliphatic polyester (A) takes place, (ii) a step of forming a substantially homogeneous solution phase consisting of the melt phase of the high-molecular-Weight aliphatic polyester (A) and the liquid phase composed of the polyalkylene glycol ether (B) and the solubilizing agent (C), (iii) a step of continuing to heat the solution phase under reduced pressure to form the cyclic ester by depolymerization and distil out the cyclic ester together with the polyalkylene glycol ether (B), and (iv) a step of recovering the cyclic ester from the distillate.

29. A process for purification of a crude cyclic ester, which comprises the steps of heating a mixture containing the crude cyclic ester (A') and a polyalkylene glycol ether (B), which is represented by the following formula (1)

(1)

where $R^1$ is a methylene group, or a straight-chain or branched-chain alkylene group with 2–8 carbons, $X^1$ is a hydrocarbon group, Y is an alkyl or aryl group with 2–20 carbons, p is an integer not smaller than 1 and when p is 2 or greater, a plurality of $R^1$ groups may be identical or different, and has a boiling point of 230–450° C. and a molecular weight of 150–450, under normal or reduced pressure in order to form a substantially homogeneous solution phase without phase separation of the components; continuing to heat the solution phase to distil out the cyclic ester (A) together with the polyalkylene glycol ether (B); and recovering the cyclic ester (A) from the distillate, wherein said polyalkylene glycol ether (B) is a polyalkylene glycol ether in which the cyclic ester is soluble in the range of 0.1–10% at 25° C.

30. The process for production according to claim 4, wherein said poly(α-hydroxycarboxylic acid) is polyglycolic acid.

* * * * *